United States Patent [19]

Moaddeb

[11] Patent Number: 5,324,325
[45] Date of Patent: Jun. 28, 1994

[54] MYOCARDIAL STEROID RELEASING LEAD

[75] Inventor: Shahram Moaddeb, Woodland Hills, Calif.

[73] Assignee: Siemens Pacesetter, Inc., Sylmar, Calif.

[21] Appl. No.: 38,564

[22] Filed: Mar. 26, 1993

Related U.S. Application Data

[63] Continuation of Ser. No. 722,025, Jun. 27, 1991, abandoned.

[51] Int. Cl.⁵ .............................................. A61N 1/05
[52] U.S. Cl. ................................... 607/120; 607/126; 607/127
[58] Field of Search ............ 128/642, 785, 786, 419 P; 607/119, 120, 121, 126, 127, 130, 131

[56] References Cited

U.S. PATENT DOCUMENTS

| | | | |
|---|---|---|---|
| H356 | 11/1987 | Stokes et al. | 128/785 |
| 3,568,660 | 3/1971 | Crites et al. | 128/2 |
| 3,680,544 | 8/1972 | Shinnick et al. | 128/2 R |
| 4,209,019 | 6/1980 | Dutcher et al. | 128/419 P |
| 4,217,913 | 8/1980 | Dutcher | 128/785 |
| 4,258,724 | 3/1981 | Balat et al. | 128/786 |
| 4,360,031 | 11/1982 | White | 128/786 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,649,938 | 3/1987 | McArthur | 128 X/419 P |
| 4,711,251 | 12/1987 | Stokes | 128/784 |
| 4,819,661 | 4/1989 | Heil, Jr. et al. | 128/786 |
| 4,819,662 | 4/1989 | Heil Jr. et al. | 128/786 |
| 4,876,109 | 10/1989 | Mayer et al. | 427/2 |
| 5,002,067 | 3/1991 | Berthelsen et al. | 128 X/642 |
| 5,003,992 | 4/1991 | Holleman et al. | 128/785 |

OTHER PUBLICATIONS

Stokes, K. B. "Preliminary Studies on a New Steroid Eluting Epicardial Electrode", *PACE*, vol. 11 (Nov. 1988), pp. 1797–1803.

*Primary Examiner*—Lee S. Cohen
*Assistant Examiner*—Samuel Gilbert
*Attorney, Agent, or Firm*—Leslie S. Miller; Harold C. Schloss

[57] ABSTRACT

A lead for delivering electrical stimulation pulses to pace the cardiac muscle and for sensing electrical signals occurring in the cardiac muscle is disclosed which as a rigid helix disposed at the extreme distal end thereof which rigid helix may be operated by the implanting physical to extend the tip of the rigid helix from a stored position within the distal end of the lead to a deployed position projecting from the distal end of the lead. The rigid helix pierces and engages the heart tissue to anchor the lead in place within the heart. The tip of the rigid helix has an axial bore therein which is filled with a therapeutic medication such as a steroid or steroid-based drug for inhibiting inflammation and promoting tissue growth. After the tip of the helical screw is disposed in the heart tissue, the therapeutic medication will be slowly eluted into the surrounding tissue, thereby minimizing the trauma of implantation and assisting in the anchoring of the lead.

20 Claims, 1 Drawing Sheet

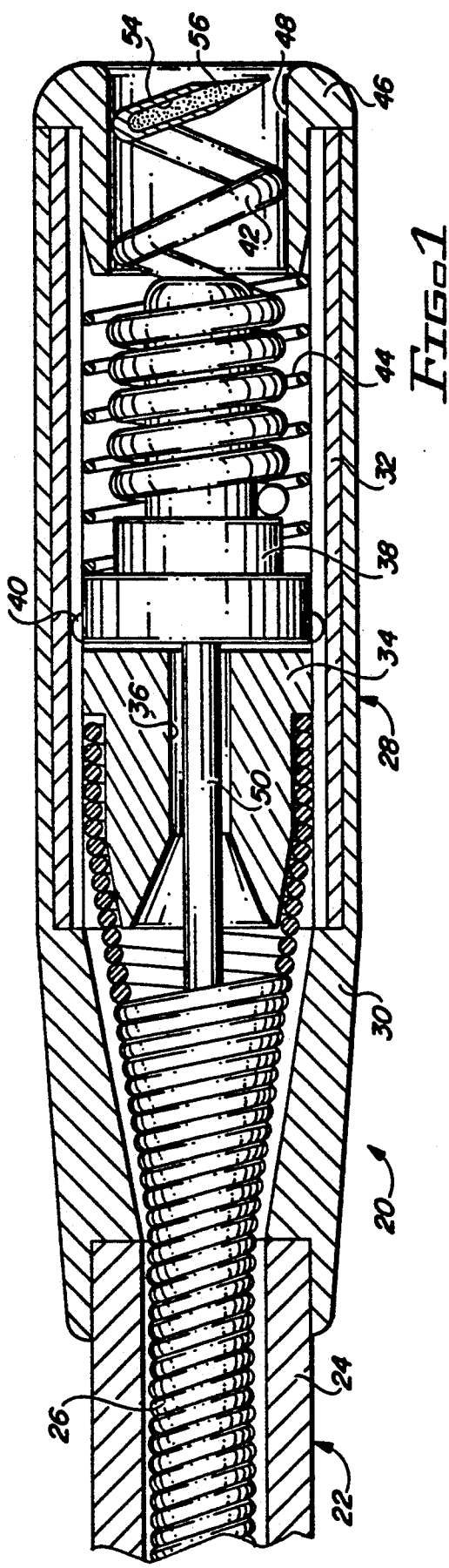
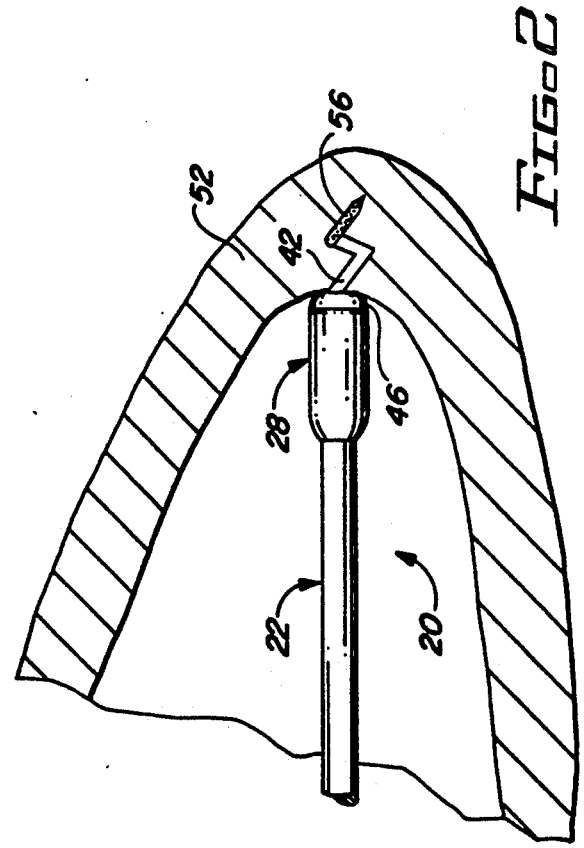

MYOCARDIAL STEROID RELEASING LEAD

This is a continuation of co-pending application Ser. No. 07/722,025 filed on Jun. 27, 1991 now abandoned.

BACKGROUND OF THE INVENTION

Field of the Invention

The present invention is directed to a screw-in type myocardial pacemaker lead, and in particular to such a lead having a steroid or steroid-based drug stored therein and means for dispensing the drug into tissue surrounding the distal end of the lead after implantation.

Various types of pacemaking leads and cardiopulmonary catheter structures are known in the art which include means for introducing a drug into the area surrounding tissue adjacent a distal end of the lead or catheter.

Catheters for drug delivery to an in vivo site with the catheter having a distal end designed to penetrate the heart wall, so that the distal end may be disposed within the heart, are described in U.S. Pat. No. 3,680,544, to Shinnick et al., and in U.S. Pat. No. 3,568,660, to Crites et al. Such catheters are primarily for use in emergency situations for introducing an externally administered drug into direct contact with the cardiac muscle, such as upon the occurrence of complete loss of cardiac output. As such, they do not include structure for storing the drug.

A combination pacing lead and drug delivery structure is disclosed in U.S. Pat. No. 4,360,031, to White. The lead disclosed in White has conventional electrical conductors for delivering pacing pulses to the heart, and also contains a channel, concentric with the conductor, through which a drug can be dispensed which exits through holes at the extreme distal end of the lead. The drug is contained within an implanted bladder, remote from the distal end of the lead, which can be filled by a percutaneous syringe.

Pacing leads which are anchored in the heart by means of tines at a distal end thereof which engage the trabeculae, and which have a cavity at the distal end of the lead in which a drug to counter undesirable interactions between the lead and tissue is contained, are disclosed in U.S. Pat. No. 4,711,251, to Stokes, and in U.S. Pat. No. 4,506,680, also to Stokes. Tined leads having tips consisting of porous or molecular sieve-forming material, with a drug being stored in and dispensed from the tip, are disclosed in U.S. Pat. No. 4,819,662, to Heil, Jr. et al.; in U.S. Pat. No. 4,606,118, to Cannon et al.; and in U.S. Pat. No. 4,577,642, to Stokes.

An epicardial lead is disclosed in U.S. Statutory Invention Registration No. H356, to Stokes et al., which lead has a barbed electrode tip with an axial bore therein. The bore, which terminates short of the tip, may have an inflammation-preventing drug stored therein. The drug is dispensed to surrounding tissue via a plurality of radial openings in the electrode, and is not dispensed directly at the electrode tip. Another epicardial drug eluting lead is described in the article "Preliminary Studies on a New Steroid Eluting Epicardial Electrode," Stokes, *PACE*, Vol. 11, pp. 1797–1803 (Nov. 1988), in the form of a helical screw-in electrode, with the lead having steroid contained in solid form located in the housing at the distal end of the lead. It is necessary for fluid to migrate into the distal end of the electrode through a porous channel to dissolve the steroid to permit the steroid to diffuse into the electrode-tissue interface.

An endocardial screw-in lead is disclosed in U.S. Pat. No. 4,876,109, to Mayer et al., which lead has having a biocompatible covering which is soluble in body fluids surrounding the fixation helix. The covering is for the purpose of shielding the helix during insertion of the lead, so that a mechanism does not have to be used to extend the helix from the distal end of the lead after insertion. Although the covering dissolves in body fluids after implantation, the covering material is not intended to therapeutically interact with the tissue.

A further screw-in pacemaker lead is disclosed in U.S. Pat. No. 4,819,661, to Heil, Jr. et al., which has a chamber open to the distal end of the lead with a matrix impregnated with a therapeutic drug being retained in the chamber.

SUMMARY OF THE INVENTION

It is an object of the present invention to provide a screw-in cardiac pacing lead which facilitates the introduction of a therapeutic medication such as an inflammation reducing agent at the direct site of traumatic engagement of the lead with heart tissue.

The above object is achieved in a lead of the type having a helix which can be operated by the physician to project from the extreme distal end of the lead to pierce and engage heart tissue to anchor the lead thereto. The extreme distal end of the helix, which pierces heart tissue, has an annular bore therein in which, in the preferred embodiment, a steroid or steroid-based drug is stored in solid form. After implantation, the steroid or steroid-based drug will slowly dissolve and disperse into surrounding cardiac tissue as a result of interaction with body fluids. Inflammation at the electrode-tissue interface may thereby be reduced, and tissue growth will be promoted which will assist in the anchoring of the lead.

DESCRIPTION OF THE DRAWINGS

These and other advantages of the present invention are best understood with reference to the drawings, in which:

FIG. 1 is a sectional side view of the distal end of a lead constructed in accordance with the principles of the present invention; and FIG. 2 is a schematic depiction of the lead of FIG. 1 anchored in heart tissue.

DETAILED DESCRIPTION OF THE PREFERRED EMBODIMENT

The distal portion of a steroid eluting lead 20 constructed in accordance with the principles of the present invention is shown in FIG. 1. While the steroid eluting lead 20 illustrated is a unipolar lead, the principles of the present invention are equally applicable to the construction and implantation of a bipolar or multipolar lead. The steroid eluting lead 20 includes a flexible cable portion 22 of standard construction having an insulating exterior 24, typically comprising a segment of tubing which is inert to body fluids, surrounding a helical conductor 26.

The flexible cable portion 22 is mechanically and electrically connected at its distal end to an electrode head structure referred to generally as 28. (A connector would be mechanically and electrically connected at the proximal end of the flexible cable portion 22 as is conventional in the art.) The electrode head structure 28 comprises a hollow electrode housing member 30 made of an insulating and body inert material. The hollow interior of the electrode housing member 30 is cylindrical, except at the proximal end of the electrode housing member 30 where it encloses the distal end of the flexible cable portion 22. Located inside the electrode housing member 30 is a hollow cylindrical interior member 32 typically made of a conductive metal material.

The helical conductor 26 extends out of the insulating exterior 24 at the distal end of the flexible cable portion 22, and is flared outwardly. A metal insert 34 is used to retain the helical conductor 26 inside the electrode head structure 28. The metal insert 34 consists of two adjacent coaxial cylindrical segments, with the distal cylindrical segment having a larger diameter than the proximal cylindrical segment. A longitudinal aperture 36 extends through the length of the metal insert 34, in communication with the interior of the helical conductor 26. The flared portion of the helical conductor 26 fits over the distal cylindrical segment of the metal insert 34, which is installed inside the interior member 32.

The distal cylindrical segment of the metal insert 34 fits in an interference fit within the interior member 32, and the flared portion of the helical conductor 26 is caught in an interference fit between the proximal cylindrical segment of the metal insert 34 and the interior of the interior member 32. The proximal end of the electrode housing member 30 encloses the distal end of the insulating exterior 24 of the flexible cable portion 22 in a sealing relationship.

Located inside the interior member 32 distal of the metal insert 34 is a reciprocating anchoring mechanism 38. The anchoring mechanism 38 consists of three adjacent coaxial cylindrical segments, with the proximal one of these cylindrical segments having a diameter slightly less than the inner diameter of the interior member 32. The intermediate cylindrical segment of the anchoring mechanism 38 has a diameter less than the diameter of the proximal cylindrical segment of the anchoring mechanism 38, and the distal cylindrical segment of the anchoring mechanism 38 has a diameter less than the diameter of the intermediate cylindrical segment of the anchoring mechanism 38.

An annular rib 40 is located around the outer circumference of the proximal cylindrical segment of the anchoring mechanism 38. This annular rib 40 closely fits the internal diameter of the interior member 32, allowing the anchoring mechanism 38 to reciprocate but with a bit of friction.

A rigid helix 42 terminating at the distal end thereof in a sharpened tip capable of piercing heart tissue has its proximal end mounted in an interference fit on the distal cylindrical segment of the anchoring mechanism 38. A spring 44 is installed inside of the interior member 32, with the proximal end of the spring 44 being mounted around the intermediate cylindrical segment of the anchoring mechanism 38.

A collar member 46 is installed in the distal end of the electrode head structure 28, with a portion of the collar member 46 being installed in an interference fit inside the interior member 32. The collar member 46 has a centrally located aperture 48 located therein, which aperture 48 is larger in diameter than the outer diameter of the rigid helix 42. The collar member 46 extends only a short distance out of the electrode housing member 30, and thus presents an annular distal portion through which pacing and sensing will be accomplished.

The distal end of the spring 44 bears on the proximal end of the collar member 46, which is fixed in an interference inside the interior member 32. Accordingly, it may be seen that the spring 44 will bear against the anchoring mechanism 38 to urge it proximally into contact with the metal insert 34. With the anchoring mechanism 38 in its fully proximal position abutting the metal insert 34 as shown in FIG. 1, the sharpened distal tip of the rigid helix 42 is fully retracted within the aperture 48 in the collar member 46. This is the position in which the rigid helix 42 will be during transvenous insertion of the steroid eluting lead 20 to place the electrode head structure 28 within the heart.

The collar member 46 at the distal tip of the electrode head structure 28 is placed by the implanting physician at the proper location within the heart. A stylet 50 is inserted into and through the helical conductor 26 from the proximal end of the steroid eluting lead 20, and through the aperture 36 in the metal insert 34. The distal end of the stylet 50 will thereby bear against the anchoring mechanism 38.

The stylet 50 may then be operated through a well known mechanism to advance the anchoring mechanism 38 and the rigid helix 42 distally within the electrode head structure 28, against the force of the spring 44. Advancing the rigid helix 42 causes it to project from the collar member 46, thereby allowing it to be screwed into heart tissue 52 as shown in FIG. 2, anchoring the electrode head structure 28 of the steroid eluting lead 20 in place.

The rigid helix 42 may or may not be electrically connected to the helical conductor 26, and thus may optionally serve the purpose of delivering electrical energy to the heart in the form of pacing pulses. Electrical isolation of the rigid helix 42, if desired, may be accomplished by making the anchoring mechanism 38 of a nonconductive material.

Referring back to FIG. 1, the extreme distal end of the rigid helix 42, at which the sharpened tip is disposed, has an annular bore 54 therein, which is open at the tip of the rigid helix 42. A therapeutic medication 56 is contained within the bore 54. The therapeutic medication 56 may preferably be in the form of a suspension in a matrix of known composition. For example, it may be compounded into a solid material such as silicone rubber, polyurethane, polyethylene, polysulphone, a ceramic material, or any other biocompatible material. In one preferred embodiment, the therapeutic medication 56 may be a steroid or steroid-based drug.

Referring once more to FIG. 2, the therapeutic medication 56 is disposed at the direct site of traumatic engagement of the tip of the rigid helix 42 with the heart tissue 52. The therapeutic medication 56 will interact with body fluids so as to diffuse into the heart tissue 52 surrounding the tip of the rigid helix 42.

If the therapeutic medication 56 is a steroid or steroid-based drug, it will act to relieve the inflammation which typically occurs at the time of implantation, and also to promote tissue growth surrounding the rigid helix 42 to assist in anchoring the steroid eluting lead 20. The bore 54 in the tip of the rigid helix 42 may contain a sufficient amount of the therapeutic medication 56 to allow it to be dispensed over an extended period of time.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A pacing lead comprising:
   a flexible cable containing at least one electrical conductor, said flexible cable having a proximal end and a distal end;
   an electrode housing member made of nonconductive material and having a proximal end and a distal end, said distal end of said flexible cable entering said electrode housing member at said proximal end of said electrode housing member;
   at least one electrode located at said distal end of said electrode housing member, said electrode being in electrical communication with said electrical conductor;
   active fixation means for actively fixing said electrode in close proximity to heart tissue, said active fixation means having a proximal end and a distal end, said proximal end of said active fixation means being connected to said electrode housing; and
   storing means for storing a therapeutic medication to be dispensed into heart tissue, said storing means being located entirely within said active fixation means and communicating with the outside of said active fixation means only at the distal end thereof.

2. A pacing lead, as defined in claim 1, wherein said active fixation means extends from said distal end of said electrode housing member.

3. A pacing lead, as defined in claim 2, wherein said electrode comprises:
   an annular member located at said distal end of said electrode housing member, said active fixation means being located at least partially within said annular member.

4. A pacing lead, as defined in claim 1, wherein said active fixation means is deployable from said distal end of said electrode housing member, said active fixation means being moveable between a first position in which it does not extend beyond said electrode, and a second position in which it extends beyond said electrode.

5. A pacing lead, as defined in claim 1, wherein said active fixation means is in electrical communication with said electrical conductor.

6. A pacing lead, as defined in claim 1, wherein said active fixation means is electrically insulated from said electrical conductor.

7. A pacing lead, as defined in claim 1, wherein said distal end of said active fixation means comprises:
   a sharpened tip.

8. A pacing lead as defined in claim 7, wherein said active fixation means comprises:
   a helix.

9. A pacing lead, as defined in claim 8, wherein said storing means additionally comprises:
   an internal bore located within said helix, said internal bore having an opening adjacent to and in communication with the exterior of said sharpened tip.

10. A pacing lead, as defined in claim 1, wherein said therapeutic medication comprises:
    steroids or steroid-based drugs.

11. A pacing lead, as defined in claim 1, wherein said therapeutic medication is compounded into a solid material.

12. A pacing lead, as defined in claim 1, wherein said therapeutic medication is compounded into a material selected from the group consisting of silicone rubber, polyurethane, polyethylene, polysulphone, and a ceramic material.

13. A pacing lead comprising:
    a flexible cable containing at least one electrical conductor, said flexible cable having a proximal end and a distal end;
    an electrode housing member made of nonconductive material and having a proximal end and a distal end, said distal end of said flexible cable entering said electrode housing member at said proximal end of said electrode housing member;
    at least one electrode located at said distal end of said electrode housing member, said electrode being in electrical communication with said electrical conductor;
    a helix having a sharpened distal tip, for actively fixing said electrode in close proximity to heart tissue, said helix having a proximal end and a distal end, said proximal end of said helix being connected to said electrode housing; and
    storing means for storing a therapeutic medication to be dispensed into heart tissue, said storing means being located entirely within said helix and communicating with the outside of said helix only at the distal end thereof.

14. A pacing lead, as defined in claim 13, wherein said storing means is in communication with said sharpened distal tip of said helix.

15. In a body implantable lead for the delivery of stimulation energy to a desired body site of the type having at least one electrode carried by said lead which is adapted for positioning adjacent to said desired body site, and an active fixation member for maintaining said electrode adjacent said desired body site, the lead and the active fixation member each having la proximal end and a distal end, the improvement wherein said lead further comprises:
    drug dispensing means for dispensing a drug, said drug dispensing means being carried by said active fixation member, including means disposed entirely within said active fixation member for storing a drug to be dispensed while allowing dispensing of said drug only at the distal end of said active fixation member to counter undesirable interactions between said lead and the body site.

16. The body implantable lead of claim 15, wherein said drug is compounded into a solid material, said solid material being carried by said lead entirely within said active fixation member.

17. A pacing lead comprising:
    a flexible cable containing at least one electrical conductor, said flexible cable having a proximal end and a distal end; and
    an anchoring and energy delivery structure having a proximal end and a distal end, said proximal end of said structure being connected to said distal end of said cable, said structure comprising:
    a rigid helix having a sharpened tip adapted to pierce heart tissue and contained within an opening in said distal end of said structure;
    means for mechanically advancing said helix to cause said helix to project from said distal end and to screw said helix into heart tissue to anchor said pacing lead; and means, contained entirely within said helix and in open communication with the outside of said helix only at said sharpened tip, for storing a therapeutic medication and for releasing said therapeutic medication directly through said sharpened tip after said helix has been screwed into heart tissue.

18. A pacing lead, as defined in claim 17, wherein said therapeutic medication is selected from the group consisting of steroids and steroid-based drugs.

19. A pacing lead comprising:

a flexible cable containing at least one electrical conductor, said flexible cable having a proximal end and a distal end; and an anchoring and energy delivery structure having a proximal end and a distal end, said proximal end of said structure being connected to said distal end of said cable, said structure comprising:

a rigid helix having a sharpened tip adapted to pierce heart tissue and contained within an opening in said distal end of said structure;

means for mechanically advancing said helix to cause said helix to project from said distal end and to screw said helix into heart tissue to anchor said pacing lead; and a bore located entirely within said helix and in open communication with the outside of said helix only at said sharpened tip of said helix, said bore containing a therapeutic drug so that after said helix has been screwed into said heart tissue said therapeutic drug is in direct contact with said heart tissue and is directly released into said heart tissue through said sharpened tip of said helix.

20. A pacing lead, as defined in claim 19, wherein said therapeutic drug is selected from the group consisting of steroids and steroid-based drugs.

* * * * *